US006786932B1

(12) United States Patent
Blackmore

(10) Patent No.: US 6,786,932 B1
(45) Date of Patent: Sep. 7, 2004

(54) FEMUR END IMPLANT

(76) Inventor: Armand N. Blackmore, 5572 Gaertner Ct., Bay City, MI (US) 48706

( * ) Notice: Subject to any disclaimer, the term of this patent is extended or adjusted under 35 U.S.C. 154(b) by 0 days.

(21) Appl. No.: 10/291,960

(22) Filed: Nov. 11, 2002

(51) Int. Cl.$^7$ .................................................. A61F 2/36
(52) U.S. Cl. ............................... 623/23.33; 623/23.15; 623/23.11; 623/20.35; 606/72
(58) Field of Search ........................... 623/20.35, 20.36, 623/22.4–22.46, 23.32–23.35, 23.11–23.15, 23.26; 606/72–75

(56) References Cited

U.S. PATENT DOCUMENTS

| 1,156,440 A | | 10/1915 | Smith |
| 1,950,799 A | | 3/1934 | Jones |
| 2,110,414 A | | 3/1938 | Bell |
| 2,502,902 A | | 4/1950 | Tofflemire |
| 2,966,907 A | | 1/1961 | Fasolino |
| 3,900,025 A | | 8/1975 | Barnes, Jr. |
| 4,263,904 A | | 4/1981 | Judet |
| 4,890,631 A | | 1/1990 | Hardy |
| 4,938,770 A | * | 7/1990 | Frey et al. ................ 623/23.15 |
| 5,020,797 A | | 6/1991 | Burns |
| 5,108,393 A | | 4/1992 | Ruffa |
| 5,190,545 A | | 3/1993 | Corsi et al. |
| 5,443,483 A | | 8/1995 | Kirsch |
| 5,462,563 A | * | 10/1995 | Shearer et al. ........... 623/20.11 |
| 5,662,653 A | | 9/1997 | Songer et al. |
| 5,665,089 A | | 9/1997 | Dall et al. |
| 5,741,259 A | | 4/1998 | Chan |
| 5,810,816 A | | 9/1998 | Roussouly et al. |
| 5,810,817 A | | 9/1998 | Roussouly et al. |
| 5,810,824 A | | 9/1998 | Chan |
| 6,280,446 B1 | | 8/2001 | Blackmore |

OTHER PUBLICATIONS

Simplex Bone Cement, Copyright 1997, Howmedia Inc. 9 pages.

* cited by examiner

Primary Examiner—David J Isabella
(74) Attorney, Agent, or Firm—Reising, Ethington, Barnes, Kisselle & Learman, P.C.

(57) ABSTRACT

A femur head implant has an oblique neck. A ball portion of a hip joint is connected to a first neck end. A femur head hollow portion is connected to a second end of the oblique neck. A tubular shell is connected to a lower end of the hollow portion. A slot in the tubular shell permits changes in the inside diameter of a femur shaft passage through the tubular shell. Screws are tightened to reduce the inside diameter and clamp the implant to a femur shaft that is received in the shaft passage and extends into the femur head hollow portion. Passages are provided in the hollow portion for the insertion of bone cement into the hollow portion and the escape of gas from the hollow portion.

12 Claims, 2 Drawing Sheets

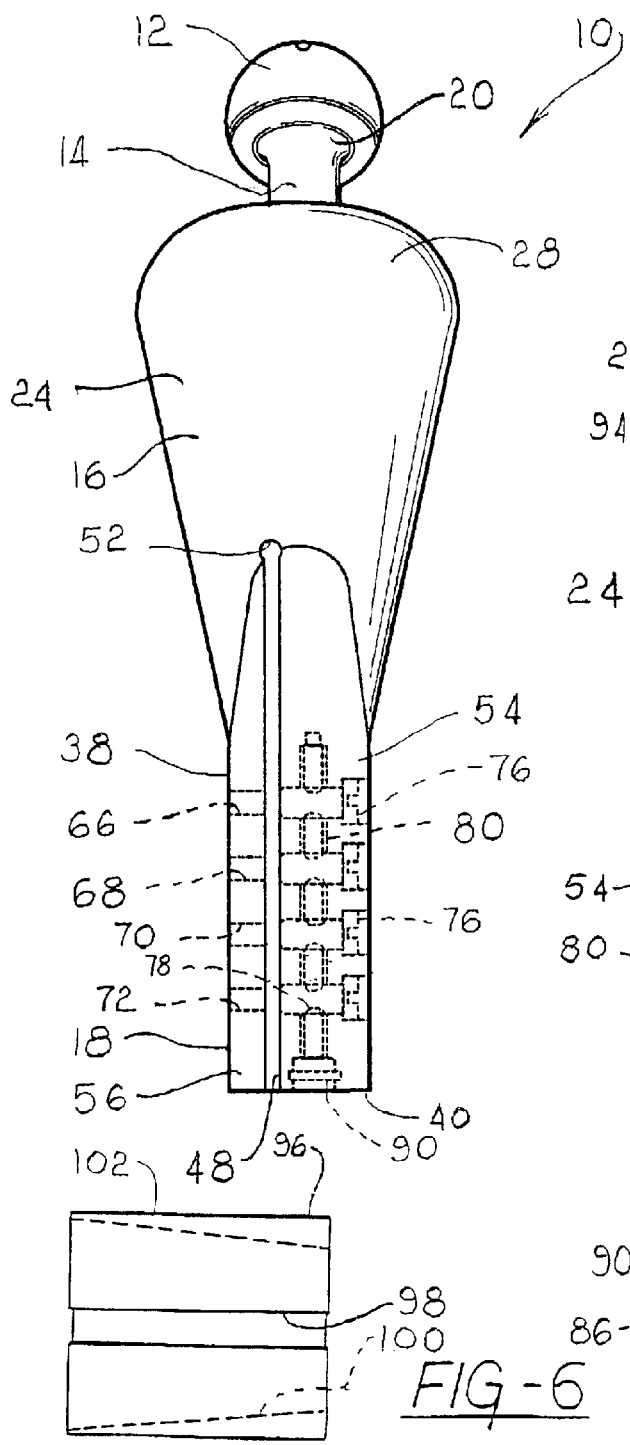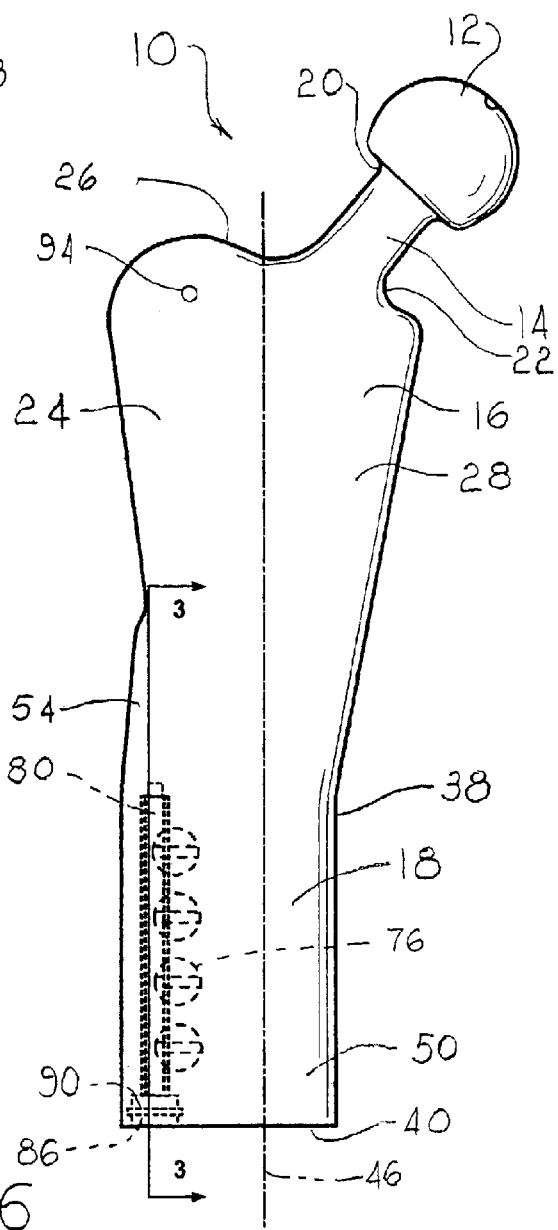

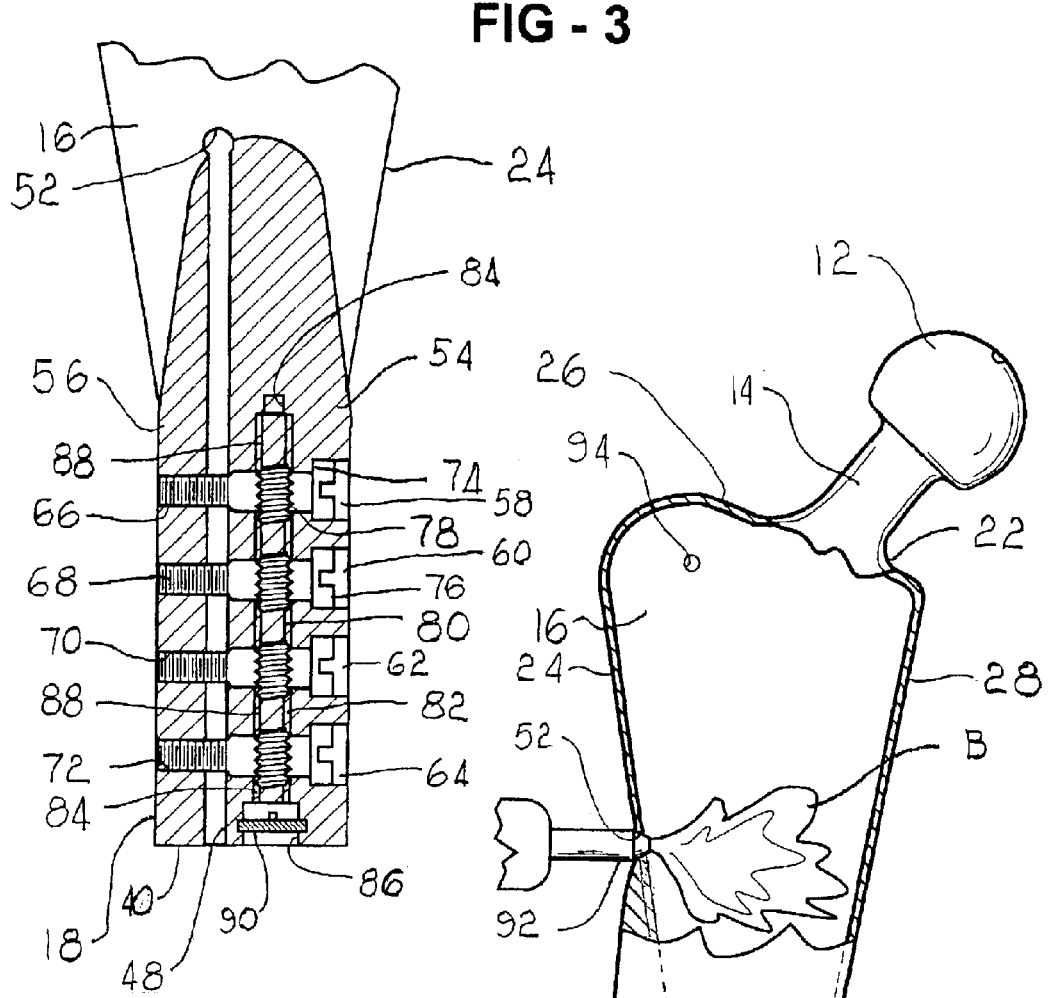
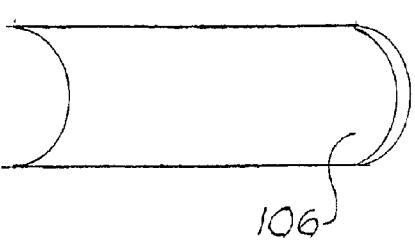

FEMUR END IMPLANT

FIELD OF THE INVENTION

The femur end implant includes a femur end joint portion, a hollow portion connected to the end joint portion and a tubular shell integral with the hollow portion and having a generally cylindrical passage that receives a femur shaft and has an adjustable inside diameter for compressing the femur shaft radially and holding the femur end joint portion in an axially and angularly fixed position relative to the femur shaft.

BACKGROUND OF THE INVENTION

Bones of the human skeleton are broken from time to time. Bones also wear out or fail due to a number of factors, such as mineral and vitamin deficiency, side effects of drugs, hard use, arthritis and other factors, both known and unknown.

Repair of the human skeleton has made significant advances in recent years. The Egyptians learned how to set some broken bones so that they could grow back together and function like they did prior to the injury. Today, artificial joints are available for hips, knees, shoulders, and wrists. It is also possible to repair some finger joints.

Skeletal injuries which change the length of some bones can be repaired in some cases. Doctors successfully make bone grafts using bone pieces from a donor individual. A splint disclosed in my U.S. Pat. No. 6,280,446 issued Aug. 28, 2001, the disclosure of which is incorporated herein by reference, can be used to return a femur to its original length when a section of the bone is destroyed or missing. A similar splint could be used on the tibia and fibula of the lower leg as well as on the humerus, ulna and radias of the arm. Hip joints that are currently used, when the oblique neck of the femur is weak, have a ball joint member connected to a metal shank. The metal shank, in some joint designs, is inserted into an axial bore formed in the upper end of the femur and anchored by an adhesive. In other joint designs, the metal shank is attached to an outside surface of the femur shaft by screws. The initial connection between the metal shank and the femur shaft works well and lasts several years if the femur shaft is in good condition at the time of implantation. The metal shank and ball joint members sometimes fail after several years of use. There are individuals that have had multiple implant replacements. During replacement of a broken joint implant in a bone such as the femur, the depth of the axial bore in the femur shaft must be bored a little deeper and a portion of the upper end of the shaft must be removed in order to obtain a satisfactory connection between the implant and the shank. When the femur shaft and the shank are connected to each other by screws, it may also be necessary to shorten the femur shaft somewhat. In both cases, the person receiving the implant ends up with a short leg. A short leg makes walking somewhat difficult. A more serious problem with a short leg is the long-term detrimental effect on other parts of the skeleton, such as the spine. Problems with the skeletal portion of the human body result in soft tissue problems eventually.

SUMMARY OF THE INVENTION

The femur head implant includes an oblique neck with a ball support end and a lower neck end. A hip joint ball is attached to the ball support end of the oblique neck. A femur head hollow portion has a hollow portion upper end that is integral with the lower neck end of the oblique neck, and a hollow portion lower end. A tubular shell has a tubular shell upper end integral with the hollow portion lower end. A generally cylindrical passage through the tubular shell, has a cylindrical passage diameter, a femur shaft axis coaxial with the generally cylindrical passage, and a tubular shell lower end. A shell slot in the tubular shell extends from the tubular shell lower end, through the tubular shell upper end, and into the femur head hollow portion. A first clamp flange is integral with the tubular shell on a first side of the shell slot. A second clamp flange is integral with the tubular shell on a second side of the shell slot. A plurality of threaded bores through the second clamp flange are each in axial alignment with one of a plurality of bores through the first clamp flange. A plurality of screws, each of which passes through one of the plurality of bores through the first clamp flange, screw into one of the plurality of threaded bores through the second clamp flange. Tightening of the plurality of screws reduces the cylindrical passage diameter and clamps the femur head implant to a femur shaft received in the generally cylindrical passage. Clamping the femur head implant to the femur shaft fixes the femur head relative to the femur shaft.

BRIEF DESCRIPTION OF THE DRAWINGS

The presently preferred embodiment of the invention is disclosed in the following description and in the accompanying drawings, wherein:

FIG. 1 is a side elevational view of the femur head implant;

FIG. 2 is a front elevational view of the femur head implant;

FIG. 3 is a sectional view taken along line 3—3 in FIG. 2 with parts broken away;

FIG. 4 is a view similar to FIG. 2 with parts broken away and showing the injection of liquid into the femur head;

FIG. 5 is a perspective view of a shim for fitting the tubular shell to a femur shaft; and FIG. 6 is an enlarged elevational view of a ring with a conical bore for fitting a conical femur shaft in a cylindrical tubular shell.

DETAILED DESCRIPTION OF THE PREFERRED EMBODIMENT

The femur head implant 10 includes a ball 12 of a ball joint, and oblique neck 14, a femur head hollow portion 16, and a tubular shell 18. The oblique neck 14 of the femur head implant 10 is substantially the same size and shape as the bone oblique neck. The oblique neck 14 is preferably solid material due to the high stresses to which it may be subjected during use. However, it would be possible to provide a bore through the oblique neck 14 or to form a hollow neck by other procedures. The ball 12, on the proximal ball support end 20 is an integral part of the oblique neck 14 as shown in the drawing. A bearing member can be connected to the outer surface of the ball 12. The bearing surface would mate with the inside of the acetabulum or a socket implant replacing the acetabulum. A bearing surface can be connected to the socket implant if desired rather than to the ball 12. The ball 12 can also be a separate member connected to the oblique neck 14 by a mechanical fastening system if desired. The separate ball 12 can be used when it is desirable to select a ball size that corresponds to the anatomy of the person receiving the implant. Any mechanical attaching system used must be highly reliable to ensure that there is no separation or movement between the ball and the oblique neck 14. The lower neck end 22 of the oblique neck 14 is integral with the femur head hollow portion 16.

The femur head hollow portion 16 is approximately the same shape as the head portion of a healthy femur. As shown in FIGS. 1, 2 and 4, the head portion 16 is somewhat the shape of a truncated cone 24 with a flat base 26. The walls 28 of the truncated cone 24, as shown in FIG. 4, are relatively thin to reduce weight and still provide the required strength. The hollow portion 16 may flex slightly like a healthy femur to cushion the ball 12 of the ball joint as well as other portions of the skeleton. Weight supported by the ball 12 is transmitted to the tubular shell 18 by the femur head hollow portion 16.

The tubular shell 18 has an upper end 38 that is integral with the tubular shell lower end 40. A substantially cylindrical passage 42 through the tubular shell 18 extends from the tubular shell lower end 44 to the tubular shell upper end 38. During use of the femur head implant 10, a femur shaft S is received in the cylindrical passage 42 and passes into the femur head hollow portion 16. The cylindrical passage has a passage center line 46 which is coaxial with the femur shaft axis. Femur shafts S are not completely cylindrical at any location along their length. The circumference of the shaft is larger at the shaft ends than it is midway between the ends. Between the ends of the femur S, the shaft has a somewhat elliptical cross section. When the tubular shell 18 is clamped to the femur shaft S, as explained below, the shell is distorted and generally conforms to the shape of the portion of the femur shaft that is within the shell.

A shell slot 48 is provided in the wall 50 of the tubular shell 18. As shown in FIG. 4, the slot 48 extends from the shell lower end 44 to an aperture 52 in the wall 28 of the femur head hollow portion 16. The aperture 52, as shown in FIG. 1, is spaced from the upper end 38 of the tubular shell 18 a little less than half the distance from the shell upper end to the lower neck end 22.

A first clamp flange 54 is provided adjacent to one side of the shell slot 48. A second clamp flange 56 is provided adjacent to a second side of the shell slot 48. Both clamp flanges 54 and 56 extend from the tubular shell lower end 44 to the aperture 52 in the wall 28 of the hollow portion 16. The flanges 54 and 56, the tubular shell 18, the femur head hollow portion 16 and the oblique neck 14 are preferably one piece. However, the flanges 54 and 56 can be separate pieces that are permanently secured to the tubular shell 18 and the femur head hollow portion 16 by a process such as electron beam welding.

The first clamp flange 54 has four bores 58, 60, 62 and 64. The second clamp flange 56 has four threaded bores 66, 68, 70 and 72. Each of the bores 58 through 64 is in axial alignment with one of the threaded bores 66 through 72. A bearing surface 74 is provided in each of the bores 58 through 64. As shown, the bearing surface 74 is perpendicular to the bore axis 46 and faces away from the adjacent threaded bore 66 through 72. The bearing surface could also be a conical surface if desired. Screws 76 pass through each bore 58 through 64 and screw into the axially aligned threaded bores 66 through 72. A worm wheel 78 is provided on each screw 76.

A worm 80 is received in a worm passage 82, has a small end journaled in a bore 84 and the first clamp flange 54, and a head end journaled in a counter bore 86. The cylindrical portions 88 permit the screws 76 to be rotated separately when the worm 80 is backed out of the worm passage 82 and a cylindrical portion is adjacent to each worm wheel 78. During attachment of the femur head implant 10, the screws 76 are rotated individually to reduce the size of the shell slot 48 and move the shell into full engagement with the femur shaft S. The worm 80 is then moved completely into the worm passage 82 and axially retained by a snap ring 90. Rotation of the worm wheel 80 in one direction rotates all of the screws 76 simultaneously in one direction to tighten the tubular shell 18 on the femur shaft S and axially and angularly fix the femur shaft relative to the femur head implant 10. Rotation of the worm 80 in another direction rotates all of the screws 76 simultaneously in another direction and releases clamping forces on the femur shaft S.

A normal femur shaft S is very strong when radially inward force is applied 360 degrees around and perpendicular to the axis of the bone. Radially outward forces on the outer wall of a femur shaft S can pull the shaft apart. The shaft S can withstand a much larger radial compression force than a radial tension force. The worm 80 is employed to ensure that all the screws 76 apply a substantially equal radially inward force on the shaft S and that an excessive force is not applied by one screw.

During implantation of the femur head implant 10, the shell slot 48 is opened if necessary to permit a portion of a femur shaft S to move radially through the slot and into the cylindrical passage 42. The femur shaft S is then moved axially toward the oblique neck 14 until the distance between the ball 12 and the knee joint is correct and the angular alignment is correct. Then the screws 76 are tightened until they start to exert a compression force on the femur shaft S. The worm 80 is then moved into engagement with all the worm wheels 78 and the snap ring 90 is inserted to axially retain the worm. The worm 80 is then rotated to simultaneously tighten all the screws 76 and fix the femur head implant 10 relative to the femur shaft S. Measurements are then made to ensure that the femur shaft S is in the correct position relative to the ball 12. If the length of the leg is incorrect, or the toes are at an incorrect angle, the worm 80 is rotated to simultaneously loosen all the screws 76, the femur shaft S is repositioned relative to the femur head implant 10 and then the worm is rotated to simultaneously tighten all the screws.

A fluid injector with a nozzle 92 is moved into the aperture 52 and fills the femur head hollow portion 16. An air vent 94 lets air out of the hollow portion 16 so that the implant 10 is substantially filled. The fluid that is injected through the nozzle 92 is a bone cement that strengthens the implant 10 and permits the growth of new bone. The fluid, as it solidifies, strengthens the femur head hollow portion 16. After the bone cement is cured, the femur head implant becomes substantially rigid like the head portion of a healthy and undamaged femur.

The femur head implant 10 can be made from a metal such as Vitallium or other stainless steel alloys, Vitallium stainless steel alloys include cobalt and chromium and are used for various devices that are implanted in humans. Other materials could be used if they have comparable strength and are compatible with the human body.

The tubular shell 18 forms a secure connection with the femur shaft S if the portion of the shaft engaged by the tubular shell is substantially cylindrical. When clamping the tubular shell 18 to a portion of the femur shaft S that is slightly conical, a secure connection is obtained by closing the shell slot 48 more at one slot end than at the other end so that the shell upper end 38 and the shell lower end 40 both firmly engage the femur shaft. The variation in the width of the shell slot 48 that is permitted is limited however. When the taper of the femur shaft S is too large to be accommodated by the narrow shell slot 48, a ring 96 with a slot 98, a conical bore 100 and a cylindrical outer surface 102, can be placed on the small diameter portion of the femur shaft S and the cylindrical outer surface is engaged by the passage 42 through the tubular shell 18. When the ring 96 has an axial length that is substantially shorter than the tubular shell 18, the shell passage 42 also engages the femur shaft. A ring 96 with an axial length about the length of the tubular shell 18 can also be used. In some cases it may be desirable to employ two spaced apart rings 96 to accommodate a femur shaft S with an irregular surface.

The femur head implant 10 is manufactured in several different sizes to accommodate the variations in the size of femurs and other bones from one person to another. To further fit the femur head implant 10 to a specific individual, a shim 106 can be inserted into the cylindrical passage 42 and positioned between one side of the shaft S and the tubular shell 18.

The implant 10 as described above is for the hip joint. By changing the ball and the shape of the femur head hollow portion 16, the implant could be attached to the lower end of the femur shaft S and form a portion of a knee joint. The implant can also be modified to attach to the humerus and form a portion of a shoulder joint. With suitable modification, the implant 10 could also form a portion of an elbow joint.

The disclosed embodiment is representative of a presently preferred form of the invention, but is intended to be illustrative rather than definitive thereof. The invention is defined in the claims.

What is claimed is:

1. An extremity bone end implant comprising:
   a neck with a neck joint end and a neck bone shaft end;
   an articulation joint portion attached to the joint end of the neck;
   a hollow portion, with a hollow portion joint end integral with the neck bone shaft end, and a hollow portion bone shaft end;
   a tubular shell with a shell joint end integral with the hollow portion bone shaft end, a generally cylindrical passage with a cylindrical passage diameter, a cylindrical passage axis, and a tubular shell bone shaft end;
   a single shell slot in the tubular shell extending from the tubular shell bone shaft end, through the shell joint end and into the hollow portion;
   a first clamp flange integral with the tubular shell on a first side of the shell slot;
   a second clamp flange integral with the tubular shell on a second side of the shell slot;
   at least one threaded bore in the second clamp flange and in axial alignment with at least one bore through the first clamp flange;
   a screw passing through the at least one bore through the first clamp flange and screwed into the at least one threaded bore in the second clamp flange, and wherein tightening the screw reduces the cylindrical passage diameter and clamps the extremity bone end implant to a bone shaft received in the generally cylindrical passage;
   a passage through a hollow portion wall for the injection of fluid into the hollow portion; and
   wherein the hollow portion is a closed chamber except for the generally cylindrical passage into the hollow portion bone shaft end, the single slot and the passage through the hollow portion wall for the injection of fluid into the hollow portion.

2. A femur head implant comprising:
   an oblique neck with a proximal ball support end and a lower neck end;
   a hip joint ball attached to the proximal ball support end of the oblique neck;
   a femur head hollow portion forming an enclosed hollow portion chamber, with a hollow portion upper end integral with the lower neck end of the oblique neck, and a hollow portion lower end;
   a tubular shell with a tubular shell upper end integral with the hollow portion lower end, a generally cylindrical passage in communication with the enclosed hollow portion chamber, with a cylindrical passage diameter, a cylindrical passage axis, and a tubular shell lower end;
   a single shell slot in the tubular shell extending from the tubular shell lower end, through the tubular shell upper end, and into the femur head hollow portion;
   a first clamp flange integral with the tubular shell on a first side of the shell slot;
   a second clamp flange integral with the tubular shell on a second side of the shell slot;
   a plurality of threaded bores through the second clamp flange, each of which is in axial alignment with one of a plurality of bores through the first clamp flange;
   a plurality of screws each of which passes through one of the plurality of bores through the first clamp flange and screws into one of the plurality of threaded bores through the second clamp flange; and
   wherein tightening the plurality of screws reduces the cylindrical passage diameter and clamps the femur head implant to a femur shaft received in the generally cylindrical passage.

3. A femur head implant, as set forth in claim 2, wherein the oblique neck, the femur head hollow portion, the tubular shell, the first clamp flange, and the second clamp flange are made from a metal.

4. A femur head implant, as set forth in claim 3, wherein the metal is a stainless steel alloy.

5. A femur head implant, as set forth in claim 4 wherein the stainless steel alloy includes cobalt and chromium.

6. A femur head implant, as set forth in claim 3, wherein the metal is a Vitallium stainless steel alloy.

7. A femur head implant, as set forth in claim 2, including a worm wheel secured to each of the plurality of screws and a worm journaled on the first clamp flange and in mesh with all of the worm wheels.

8. A femur head implant, as set forth in claim 7, wherein the worm is journaled in a worm bore in the first clamp flange and is axially fixed in the worm bore.

9. A femur head implant, as set forth in claim 8, including a snap ring mounted in a snap ring groove in the worm bore to limit axial movement of the worm in the worm bore.

10. A femur head implant, as set forth in claim 2, including a passage through a hollow portion wall of the femur head hollow portion, for the injection of a fluid into the femur head hollow portion.

11. A femur head implant, as set forth in claim 2, including a plurality of passages through a hollow portion wall of the femur head hollow portion for the injection of a fluid into the femur head hollow portion and for the escape of gases from the femur head hollow portion.

12. A femur head implant comprising:

an oblique neck with a proximal ball support end and a lower neck end;

a hip joint ball attached to the proximal ball support end of the oblique neck;

a femur head hollow portion, with a hallow portion wall of impervious thin metal, a hollow portion upper end a femur head hollow portion, with a hallow portion wall of impervious thin metal, a hollow portion upper end integral with the lower neck end of the oblique neck, and a hollow portion lower end;

a tubular shell with a tubular shell upper end integral with the hollow portion lower end, a generally cylindrical passage with a cylindrical passage diameter, a cylindrical passage axis, and a tubular shell lower end;

a shell slot in the tubular shell extending from the tubular shell lower end, through the tubular shell upper end, and into the femur head hollow portion;

a first clamp flange integral with the tubular shell on a first side of the shell slot;

a second clamp flange integral with the tubular shell on a second side of the shell slot;

a plurality of threaded bores through the second clamp flange, each of which is in axial alignment with one of a plurality of bores through the first clamp flange;

a plurality of screws each of which passes through one of the plurality of bores through the first clamp flange and screws into one of the plurality of threaded bores through the second clamp flange;

wherein tightening the plurality of screws reduces the cylindrical passage diameter, clamps the femur head implant to a femur shaft received in the generally cylindrical passage and closes the generally cylindrical passage from the first side of the shell slot to the second side of the shell slot;

at least one passage through the hollow portion wall of the femur head hollow portion, for the injection of a fluid into the femur head hollow portion; and at least one air passage through the hollow portion wall for the escape of gases from the femur head hollow portion.

* * * * *